US00PP18225P2

(12) United States Plant Patent
Schoenmakers

(10) Patent No.: US PP18,225 P2
(45) Date of Patent: Nov. 20, 2007

(54) *FITTONIA* PLANT NAMED 'PINK DIAMOND'

(50) Latin Name: *Fittonia verschaffeltii*
Varietal Denomination: Pink Diamond

(75) Inventor: Kees Schoenmakers, Haaren (NL)

(73) Assignee: Schoenmakers Tropische Potcultures VoF, Haaren (NL)

( * ) Notice: Subject to any disclaimer, the term of this patent is extended or adjusted under 35 U.S.C. 154(b) by 19 days.

(21) Appl. No.: 11/324,434

(22) Filed: Jan. 3, 2006

(51) Int. Cl.
*A01H 5/00* (2006.01)

(52) U.S. Cl. ..... Plt./373

(58) Field of Classification Search ..... Plt./263, Plt./373
See application file for complete search history.

(56) References Cited

PUBLICATIONS

GTITM UPOVROM Citation for 'Pink Diamond' as per QZ PBR 20041487; Sep. 10, 2004.*
GTITM UPOVROM Citation for 'Pink Diamond' as per NL PBR FTN0014; Jan. 31, 2000.*

* cited by examiner

*Primary Examiner*—Kent Bell

(57) ABSTRACT

A new cultivar of *Fittonia* plant named 'Pink Diamond' that is characterized by dark pink leaf veins, wavy green leaf margins and broad ovate to elliptic leaves.

1 Drawing Sheet

Botanical classification: *Fittonia verschaffeltii.*
Variety denomination: 'Pink Diamond'.

BACKGROUND OF THE INVENTION

The present invention relates to a new and distinct cultivar of *Fittonia* plant botanically known as *Fittonia verschaffeltii* and hereinafter referred to by the cultivar name 'Pink Diamond'.

The new cultivar was discovered by the inventor in a cultivated area of Haaren, The Netherlands in September 1999. 'Pink Diamond' was discovered as a naturally occurring whole plant mutation of *Fittonia verschaffeltii* 'Anne' (not patented).

Asexual reproduction by terminal cuttings of the new cultivar 'Pink Diamond' was first done in October 1999 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Fittonia* cultivar 'Pink Diamond'.

1. *Fittonia* 'Pink Diamond' exhibits dark pink leaf veins.
2. *Fittonia* 'Pink Diamond' exhibits wavy green leaf margins.
3. *Fittonia* 'Pink Diamond' exhibits broad ovate to elliptic leaves.

The closest comparison cultivar is *Fittonia* 'White Anne' (not patented). The new cultivar *Fittonia* 'Pink Diamond' is distinguishable from *Fittonia* 'White Anne' by the following characteristics:

1. 'Pink Diamond' exhibits dark pink leaf veins. The leaf veins of 'White Anne' are white.

The new cultivar *Fittonia* 'Pink Diamond' is distinguishable from the parent plant *Fittonia* 'Anne' by the following characteristics:

1. 'Pink Diamond' has dark pink leaf veins. The leaf veins of 'Anne' are light pink.

BRIEF DESCRIPTION OF THE DRAWING

The accompanying photograph illustrates the distinguishing traits of *Fittonia* 'Pink Diamond'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Fittonia* cultivar named 'Pink Diamond'. Data was collected in Haaren, The Netherlands from 12 week old greenhouse grown plants in 8.5 cm. containers. The time of year was Fall and the average temperature was 24 degrees Centigrade during the day and 22 degrees Centigrade at night. No photoperiodic treatments were used. Color determinations are in accordance with The Royal Horticultural Society Colour Chart 2001 edition, except where general color terms of ordinary dictionary significance are used. The growing requirements are similar to the species. 'Pink Diamond' has not been tested under all possible conditions and phenotypic differences may be observed with variations in environmental, climatic, and cultural conditions, however, without any variance in genotype.

Botanical classification: *Fittonia verschaffeltii* 'Pink Diamond'.
Use: Ornamental.

Parentage: 'Pink Diamond' is a naturally occurring whole plant mutation of *Fittonia verschaffeltii* 'Anne'.
Vigor: Moderate.
Growth rate: Moderate.
Growth habit: Broad spreading, upright.
Plant shape: Flattened globose.
Suitable container size: 8.5 cm. diameter container.
Height: Average 6.6 cm.
Width: Average 9.9 cm.
Hardiness: USDA Zone 10.
Propagation: Terminal cuttings.
Time to initiate roots: Approximately 21 days to produce roots on an initial cutting at 24° Centigrade.
Time to produce a rooted cutting: Approximately 35 days to produce a rooted cutting at 24° Centigrade.
Crop time: 12 weeks.
Root system: Fine and fibrous.
Stem:
*Branching habit.*—Moderately branching.
*Average number of lateral branches.*—2.
*Pinching.*—No.
*Lateral branch diameter.*—2.5 mm. in diameter, thickened at the nodes, 3 mm in diameter.
*Lateral branch length.*—3.7 cm. in length.
*Lateral branch color.*—200D.
*Stem color.*—200C to 200D.
*Pubescence.*—Dense, length 1.2 mm, color N155A.
*Internode length.*—1.3 mm. between nodes.
*Internode color.*—143B.
*Shape.*—Rounded.
*Surface.*—Dull.
*Stem strength.*—Moderate to strong.
Foliage:
*Leaf arrangement.*—Opposite.
*Compound or single.*—Single.
*Leaf shape.*—Broad obovate to elliptic.
*Leaf apex.*—Broad acute to rounded.
*Leaf base.*—Truncate to obtuse.
*Leaf texture.*—Slightly glossy and slightly rugose with furrowed venation.
*Leaf length.*—Average 5.9 cm. in length.
*Leaf width.*—3.6 cm. in width.
*Quantity of leaves per lateral branch.*—Average 6.
*Pubescence.*—Short hairs on margins and main veins, 0.2 mm. in length, N155A.
*Leaf margin.*—Wavy.
*Vein pattern.*—Pinnate.
*Young leaf color,* (*upper surface*).—141A, margins 139A.
*Young leaf color,* (*lower surface*).—138A.
*Mature leaf color,* (*upper surface*).—139A.
*Mature leaf color,* (*lower surface*).—138B.
*Vein color* (*upper surface*).—53B, margins 53C.
*Vein color* (*lower surface*).—144B to 144C.
*Leaf attachment.*—Petiolate.
*Petiole dimensions.*—Average 1 cm. in length, 2 mm. in diameter, 1.5 mm. in height.
*Petiole color* (*upper surface*).—177B.
*Petiole color* (*lower surface*).—144C to 144D to 145A.
*Durability of foliage to stress.*—High.
Flowers: Flowers have not been observed.
Disease and insect resistance: Plants of the new *Fittonia* have not been observed for disease or insect resistance.

It is claimed:

1. A new and distinct variety of *Fittonia* plant named 'Pink Diamond' as described and illustrated.

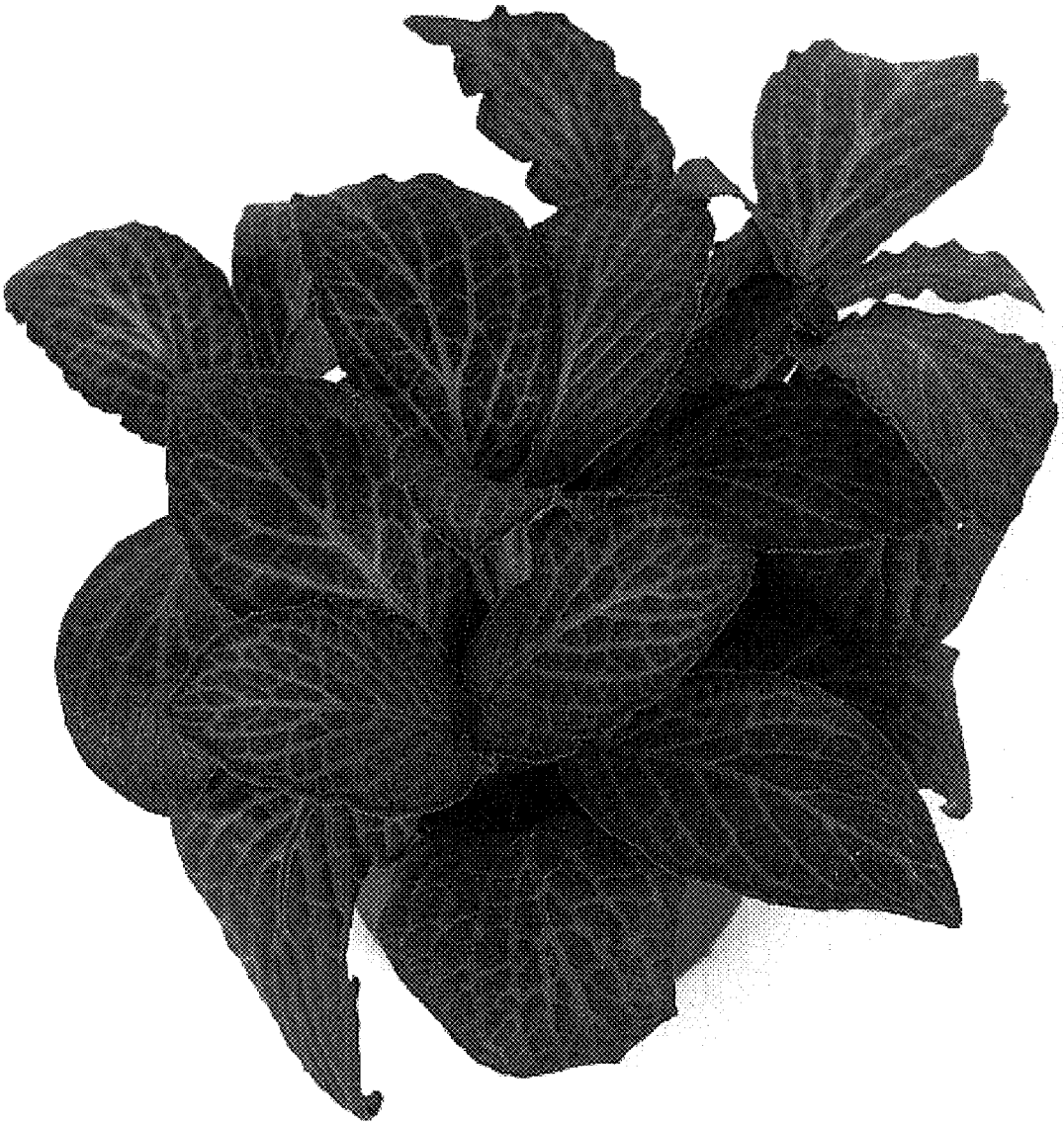

* * * * *